(12) United States Patent
Raffel et al.

(10) Patent No.: US 7,534,418 B2
(45) Date of Patent: May 19, 2009

(54) IMAGING AGENTS

(75) Inventors: David M. Raffel, Ann Arbor, MI (US); Yong-Woon Jung, Ann Arbor, MI (US); David L. Gildersleeve, Ypsilanti, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 775 days.

(21) Appl. No.: 11/009,923

(22) Filed: Dec. 10, 2004

(65) Prior Publication Data

US 2006/0127309 A1 Jun. 15, 2006

(51) Int. Cl.
*A61K 51/00* (2006.01)
*A61M 36/14* (2006.01)

(52) U.S. Cl. .................... 424/1.81; 424/1.11; 424/1.65; 424/1.85; 424/1.89; 424/9.1; 424/9.4

(58) Field of Classification Search ................ 424/1.11, 424/1.65, 1.81, 1.85, 1.89, 9.1, 9.3, 9.4, 9.5, 424/9.6, 9.7, 9.8
See application file for complete search history.

(56) References Cited

U.S. PATENT DOCUMENTS

| | | | |
|---|---|---|---|
| 4,584,187 A | 4/1986 | Wieland | |
| 4,622,217 A | 11/1986 | Wieland | |
| 4,864,138 A | 9/1989 | Mullani | |
| 5,451,789 A | 9/1995 | Wong | |
| 5,453,623 A | 9/1995 | Wong | |
| 6,674,083 B2 | 1/2004 | Tanaka | |
| 6,822,240 B2 | 11/2004 | Franckee | |
| 7,122,172 B1* | 10/2006 | Graupner | 424/9.42 |
| 7,141,234 B1* | 11/2006 | Collins et al. | 424/9.2 |

OTHER PUBLICATIONS

Berry, C.R. et al., "Imaging of Pheochromocytoma in 2 Dogs Using p-[18F]Fluorobenzylguanidine," (2002) Vet. Radiol., Ultrasound 43: 183-186.
Bolster et al., "Synthesis of DL-[1-11 C]Methionine," Appl., Radiat. Isot. 1986 (37): 1069-70.
Comar et al., "Labelling and Metabolism of Methionine-Methyl-11C", Eur. J. Nucl. Med. 1976 (1):11-14.
Gambhir, et al. (1989) "Simple Noninvasive Quantification Method for Measuring Myocardial Glucose Utilization in Humans Employing Positron Emission Tomography and fluorine- 18 Deoxyglucose" J. Nucl. Med. 30:359-366.
Shepp, L.A., and Vardi, Y., "Maximum Likelihood Reconstruction for Emission Tomography," IEEE Trans. Med. Imaging 1982; 2:113-122.
Ilias, I. et al., "Superiority of 6-[18F]-Fluorodopamine Positron Emission . . . ", (2003) The Journal of Clinical Endocrinology & Metabolism, 88:4083-4087.
Lange, Kenneth and Carson, Richard, "EM Reconstruction Algorithms for Emission and Transmission Tomography,"Journal of Computer Assisted Tomography, 1984; 8(2):306-316.
Keen et al., In Vivo Cerebral Protein Synthesis Rates with Leucyl-Transfer RNA . . . , Journal of Cerebral Blood Flow Metabolilsm, 1989 (9):429-45.
Kline, et al.: "Myocardial Imaging in Man with [123 1]- Meta-Iodobenzylguanidine," J. Nucl. Med. 22: 129-132, 1981.
Lynn, et al., "Portrayal of Pheochromocytoma and Normal Human Adrenal Medulla by m-[I-123]-iodobenzylguanidine", J. Nucl. Med., vol. 25, vol., 436-440 (1984).
Patlak, C.S. and Blasberg, R.G., "Graphical Evaluation of Blood-to-Brain Transfer Constants from Multiple-Time Uptake Data. Generalizations," (1985) The Journal of Cerebral Blood Flow and Metabolism, 5: 584-590.
Shulkin, B.L. et al., "Pheochromocytomas: Imaging with 2-[Fluorine-18]fluoro-2-deoxy-D-glucose PET", (1999) Radiology 212:35-41.
Shulkin, B.L. et al. "PET Hydroxyephedrine Imaging of Neuroblastoma" (1996) J. Nucl. Med. 37:16-21.
Sisson, et al., Scintigraphic Localization of Pheochromocytoma, New Eng. J. Med., vol. 305, pp. 12-17, (1981).
Valk, et al: "Spectrum of Pheochromocytoma in Multiple Endocrine Neoplasia: A Scintigraphic Portrayal Using . sup.131 I-Metalodobenzylguanidine," Ann. Intern. Med., vol. 94, pp. 762-767 (1981).
Westerberg, G. and Langstrom, B., Synthesis of meta-Iodobenzyl [11C]Guanidine (1997) J. Labeled Compds. Radiopharm. 39:525-529.
Wieland, et al: "Myocardial Imaging with a Radioiodinated Norepinephrine Storage Analog," J. Nucl. Med. 22:22-31, 1981.
Wiesel et al. "The Transport of Tyrosine into the Human Brain as Determined with L-[1-11C]Tyrosineand PET", J. Nucl. Med. 1991 (32):2041-49.
Shulkin, B.L. et al. "PET Scanning with Hydroxyephedrine: An Approach to the Localization of Pheochromocytoma" (1992) 1. Nucl. Med. 33:1125-1131.

* cited by examiner

*Primary Examiner*—D. L Jones
(74) *Attorney, Agent, or Firm*—Casimir Jones SC

(57) ABSTRACT

The present invention provides novel compounds that find use as imaging agents within nuclear medicine applications (e.g., PET imaging and SPECT imaging). The present invention also provides imaging compositions for use within nuclear medicine applications. Additionally, the present invention provides methods of imaging.

11 Claims, 7 Drawing Sheets

IMAGING AGENTS

This invention was supported in part with NIH grant EB000273. The United States government may have rights in this invention.

FIELD OF THE INVENTION

The present invention provides novel compounds that find use as imaging agents within nuclear medicine applications (e.g., PET imaging and SPECT imaging). The present invention also provides imaging compositions for use within nuclear medicine applications. Additionally, the present invention provides methods of imaging.

BACKGROUND

Medical radionuclide imaging (e.g., Nuclear Medicine) is a key component of modern medical practice. This methodology involves the administration, typically by injection, of tracer amounts of a radioactive substance (e.g., radiotracer agents, radiotherapeutic agents, and radiopharmaceutical agents), which subsequently localize in the body in a manner dependent on the physiologic function of the organ or tissue system being studied. The radiotracer emissions, most commonly gamma photons, are imaged with a detector outside the body, creating a map of the radiotracer distribution within the body. When interpreted by an appropriately trained physician, these images provide information of great value in the clinical diagnosis and treatment of disease. Typical applications of this technology include detection of coronary artery disease (e.g., thallium scanning) and detection of cancerous involvement of bones (e.g., bone scanning). The overwhelming bulk of clinical radionuclide imaging is performed using gamma emitting radiotracers and detectors known as "gamma cameras."

Recent advances in diagnostic imaging, such as magnetic resonance imaging (MRI), computerized tomography (CT), single photon emission computerized tomography (SPECT), and positron emission tomography (PET) have made a significant impact in cardiology, neurology, oncology, and radiology. Although these diagnostic methods employ different techniques and yield different types of anatomic and functional information, this information is often complementary in the diagnostic process.

Imaging agents are generally classified as either being diagnostic or therapeutic in their application. Although diagnostic imaging agents have historically been a mainstay in the nuclear pharmacy industry, during the past decade there has been increased interest in the development and use of therapeutic radiotherapeutic imaging agents. This shift in focus has been elicited primarily from research involving combining radioactive isotopes with sophisticated molecular carriers. Because of radiation's damaging effect on tissues, it is important to target the biodistribution of radiopharmaceuticals as accurately as possible. Generally speaking, PET uses imaging agents labeled with the positron-emitters such as $^{18}$F, $^{11}$C, $^{13}$N and $^{15}$O, $^{75}$Br, $^{76}$Br and $^{124}$I, SPECT uses imaging agents labeled with the single-photon-emitters such as $^{201}$Tl, $^{99m}$Tc, $^{123}$I, and $^{131}$I.

In the art, glucose-based and amino acid-based compounds have been used as imaging agents. Amino acid-based compounds are more useful in analyzing tumor cells, due to their faster uptake and incorporation into protein synthesis. Of the amino acid-based compounds, $^{11}$C- and $^{18}$F-containing compounds have been used with success. $^{11}$C-containing radiolabeled amino acids suitable for imaging include, for example, L-[1-$^{11}$C]leucine (Keen et al. J. Cereb. Blood Flow Metab. 1989 (9):429-45; herein incorporated by reference in its entirety), L-[1-$^{11}$C]tyrosine (Wiesel et al. J. Nucl. Med. 1991 (32):2041-49; herein incorporated by reference in its entirety), L-[methyl-$^{11}$C]methionine (Comar et al. Eur. J. Nucl. Med. 1976 (1):11-14; herein incorporated by reference in its entirety) and L-[1-$^{11}$C]methionine (Bolster et al. Appl. Radiat. Isot. 1986 (37):1069-70; herein incorporated by reference in its entirety).

PET involves the detection of gamma rays in the form of annihilation photons from short-lived positron emitting radioactive isotopes including, but not limited to $^{18}$F with a half-life of approximately 110 minutes, $^{11}$C with a half-life of approximately 20 minutes, $^{13}$N with a half-life of approximately 10 minutes and $^{15}$O with a half-life of approximately 2 minutes, using the coincidence method.

For PET imaging studies of cardiac sympathetic innervation, carbon-11 ($^{11}$C) labeled compounds such as [$^{11}$C]meta-hydroxyephedrine (HED) are frequently used at major PET centers that have in-house cyclotrons and radiochemistry facilities. However, recently the nuclear medicine market has seen a substantial increase in stand-alone PET imaging centers that do not have cyclotrons that primarily use 2-[$^{18}$F]fluoro-2-deoxy-D-glucose (FDG) for PET imaging of cancerous tumors.

SPECT, on the other hand, uses longer-lived isotopes including but not limited to $^{99m}$Tc with a half-life of approximately 6 hours and $^{201}$Tl with a half-life of approximately 74 hours. However, the resolution in present SPECT systems is even lower than that presently available in PET systems.

Radio-iodinated meta-iodobenzylguanidine (MIBG) is a radiotracing agent that is used, for example, in nuclear medicine imaging studies of sympathetic nerve fibers in the human heart. Studies with MIBG allow clinicians to map the regional distribution of nerve fibers in the heart using imaging devices found in all nuclear medicine clinics. MIBG is also used for diagnostic imaging and radiotherapy of adrenergic tumors, such as neuroblastoma and pheochromocytoma.

A need exists for improved PET and SPECT imaging agents. In particular, presently available PET imaging agents (e.g., HED, FDA, EPI) have cellular uptake rates that are too fast for quantitative kinetic analyses to succeed. Furthermore, compounds such as HED have relatively short cellular retention times. Such kinetic properties compromise physiological measurements. For example, presently available PET imaging agents cannot detect nerve losses until it is severe. As such, a need exists for PET imaging agents with (1) a slower cellular uptake rate; and (2) a long cellular retention time. Additionally, a need exists for improved SPECT imaging agents with longer retention times.

SUMMARY

The present invention provides novel compounds that find use as imaging agents within nuclear medicine applications (e.g., PET imaging and SPECT imaging). The present invention also provides imaging compositions for use within nuclear medicine applications. Additionally, the present invention provides methods of imaging organs and tissues. Such compounds and uses are described throughout the present application and represent a diverse collection of compositions and applications.

Experiments conducted during the development of the present invention identified a series of compounds finding use as imaging agents (e.g., radiotracer agents, radiotherapeutic agents, and radiopharmaceutical agents) for nuclear medicine application (e.g., SPECT and PET). The identified compounds generally include radio-labeled phenethylguanidine structures and related derivatives. Certain preferred embodiments and uses are described below. The present invention is not limited to these particular embodiments and uses.

In certain embodiments, the present invention provides a compound selected from the group consisting of (−)-β-hydroxyphenethylguanidine, para-methoxy-phenethylguanidine, meta-hydroxyphenethylguanidine, para-hydroxyphenethylguanidine, 3,4-dihydroxyphenethylguanidine, "N-guanyl-meta-octopamine", "N-guanyl-norepinephrine", "N-guanyl-(−)-metaraminol", meta-fluorophenethylguanidine, para-fluorophenethylguanidine, ortho-fluorophenethylguanidine, para-fluoro-meta-hydroxy-phenethylguanidine, ortho-fluoro-meta-hydroxy-phenethylguanidine, meta-iodophenethylguanidine, and para-hydroxy-meta-iodo-phenethylguanidine. In preferred embodiments, the compound is a radio-labeled compound. In some preferred embodiments, the radio-label is selected from the group consisting of $^{11}C$ and $^{14}C$. In preferred embodiments, the fluoro is $^{18}F$. In other preferred embodiments, the iodo is selected from the group consisting of $^{131}I$ and $^{123}I$ and $^{124}I$. In preferred embodiments, all stereoisomers for each described compound are contemplated.

In certain embodiments, the present invention provides a radio-labeled compound comprising the following structure:

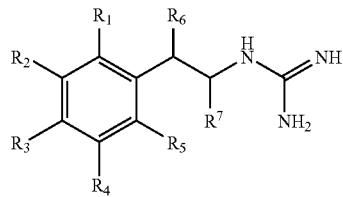

wherein R1, R2, R3, R4 and R5 are the same or different and are selected from the group consisting of H, halogen, hydroxyl, guanyl, methoxy, methyl, amino, and nitro, wherein R6 is selected from the group consisting of H and hydroxyl, and wherein R7 is H or $CH_3$. In preferred embodiments, the radio-labeled compound is selected from the group consisting of [$^{11}C$](−)-β-hydroxyphenethylguanidine, [$^{11}C$]para-methoxy-phenethylguanidine, [$^{11}C$]meta-hydroxyphenethylguanidine, [$^{11}C$]para-hydroxyphenethylguanidine, [$^{11}C$]3,4-dihydroxyphenethylguanidine, "N-[$^{11}C$]guanyl-meta-octopamine", "N-[$^{11}C$]guanyl-norepinephrine", "N-[$^{11}C$]guanyl-(−)-metaraminol", [$^{11}C$]meta-fluorophenethylguanidine, [$^{11}C$]para-fluorophenethylguanidine, [$^{11}C$]ortho-fluorophenethylguanidine, [$^{11}C$]para-fluoro-meta-hydroxy-phenethylguanidine, [$^{11}C$]ortho-fluoro-meta-hydroxy-phenethylguanidine, [$^{11}C$]meta-iodophenethylguanidine, and [$^{11}C$]para-hydroxy-meta-iodo-phenethylguanidine. In preferred embodiments, the halogen is selected from the group consisting of $^{18}F$, $^{211}At$, $^{76}Br$, $^{131}I$, and $^{123}I$. In other preferred embodiments, the present invention provides an imaging composition comprising the radio-labeled compound.

In certain embodiments, the present invention provides a method of imaging an organ comprising: applying a radio-labeled pharmaceutical composition to a subject, wherein the radio-labeled pharmaceutical composition comprises the following structure:

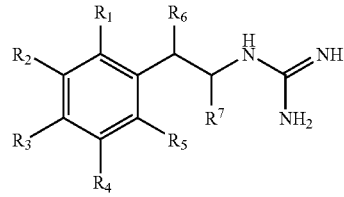

wherein R1, R2, R3, R4 and R5 are the same or different and are selected from the group consisting of H, halogen, hydroxyl, guanyl, methoxy, methyl, amino, and nitro, wherein R6 is selected from the group consisting of H and hydroxyl, and wherein R7 is H or $CH_3$; and detecting gamma radiation emitted by the pharmaceutical composition and forming an image therefrom. In preferred embodiments, the radiolabel is selected from the group consisting of $^{11}C$ and $^{14}C$. In other preferred embodiments, the halogen is selected from the group consisting of $^{18}F$, $^{76}Br$, $^{211}At$, $^{131}I$ and $^{123}I$. In some preferred embodiments, the organ is selected from the group consisting of the heart, adrenal medulla, and tumors of the adrenal medulla. In yet other preferred embodiments, the imaging is PET imaging and/or SPECT imaging.

DETAILED DESCRIPTION

Figure 1:
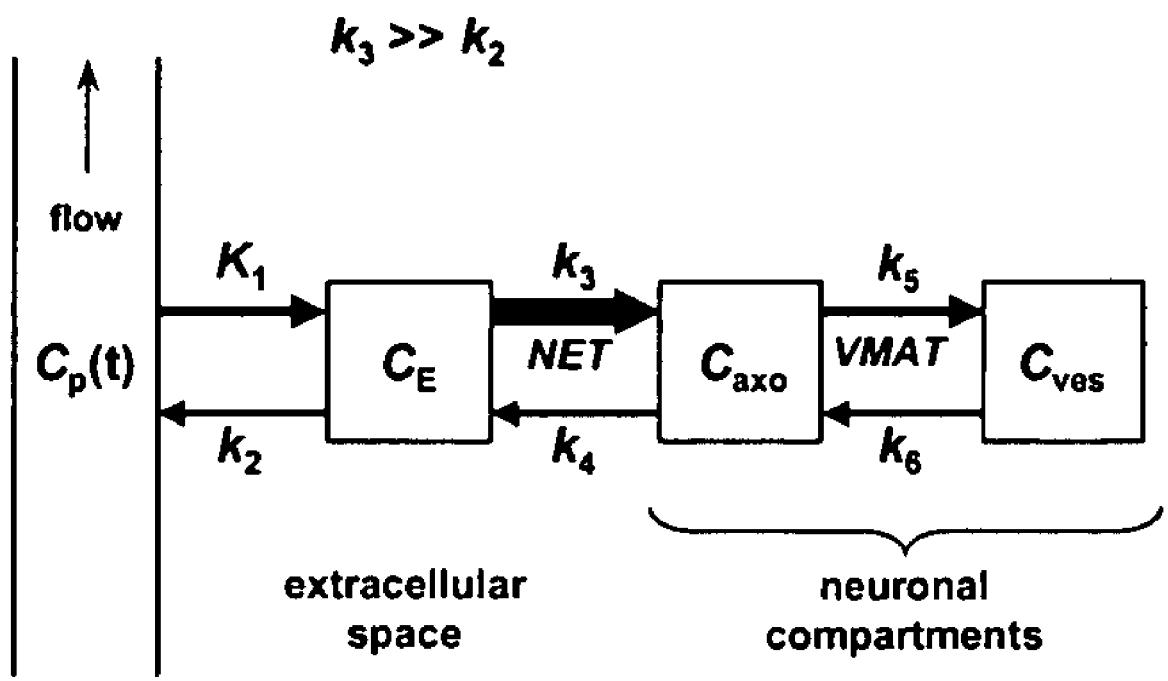
FIG. 1 shows a comprehensive model of HED kinetics. Arrow thicknesses indicate magnitudes of rate constants.

The present invention provides novel compounds that find use as imaging agents within nuclear medicine applications (e.g., PET imaging and SPECT imaging). The present invention also provides imaging compositions for use within nuclear medicine applications. Additionally, the present invention provides methods of imaging organs. Such compounds and uses are described throughout the present application and represent a diverse collection of compositions and applications.

Exemplary compounds and methods of the present invention are described in more detail in the following sections: I. Radiotracing Agents; and II. Uses of Radiotracing Agents.

I. Radiotracing Agents

Nuclear Radiology is a sub-specialty of Radiology in which radiotracing agents (e.g., compounds containing radioactive forms of atoms) are introduced into the body for the purpose of imaging, evaluating organ function, or localizing disease or tumors. Radiolabelled compounds are used, for example, for both tumor detection and tumor therapy. Many tumor cells have a higher density of cell receptors for various circulating compounds than do non-tumor cells; e.g., endocrine tumors show a high density of cell surface receptors for somatostatin, and brain gliomas show a high density of receptors for epidermal growth factor. Thus a radiolabeled compound that binds to these cellular receptors preferentially binds to the tumor cells. Additionally, angiogenesis, the formation of new blood vessels from established microvasculature, is a critical process for tumor growth. Primary tumors and metastases will not grow beyond 2 mm in diameter without an enhanced vascular supply. Angiogenic cells also have a higher density of cell receptors for various circulating compounds than do non-angiogenic vascular tissue; e.g., receptors for both somatostatin and vascular endothelial growth factor are higher in angiogenic tissue. Thus a tumor can also be detected by radiolabeled compounds binding to the angiogenic cells that are closely associated with the tumor cells.

The present invention provides new compounds useful as radiotracing agents. In preferred embodiments, the new compounds are structurally related to meta-iodobenzylguanidine (MIBG), and possess kinetic properties superior to MIBG for nuclear medicine applications. In particular, the radiotracing agents of the present invention provide a slower cellular uptake rate and a longer cellular retention length. In preferred embodiments, the present invention provides radiolabeled phenethylguanidines. These compounds can be radiolabeled with several radioisotopes, including, but not limited to, radio-halogens such as iodine-123 ($^{123}$I) for single photon imaging (e.g., SPECT imaging), iodine-131 ($^{131}$I) for radiotherapy of adrenergic tumors, and carbon-11 ($^{11}$C) or fluorine-18 ($^{18}$F) for positron emission tomography imaging (e.g., PET imaging).

Phenethylguanidines differ from benzylguanidines in that they have an additional carbon atom in the side chain of the molecule. The two-carbon side chain structure of phenethylguanidines is similar to that of norepinephrine (NE), the endogenous neurotransmitter of sympathetic neurons in the heart:

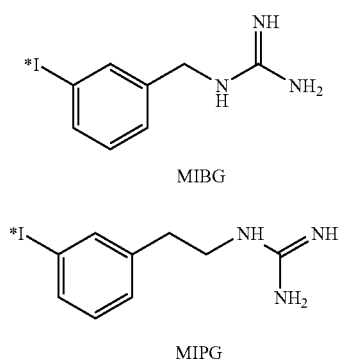

MIBG

MIPG

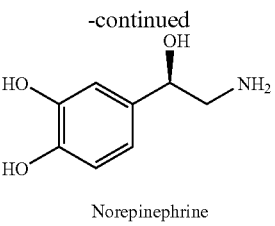

Norepinephrine

Additional exemplary compounds of the invention include, but are not limited to, (−)-β hydroxyphenethylguanidine, para-methoxy-phenethylguanidine, meta-hydroxyphenethylguanidine, para-hydroxyphenethylguanidine, 3,4-dihydroxyphenethylguanidine, "N-guanyl-meta-octopamine", "N-guanyl-norepinephrine", "N-guanyl-(−)-metaraminol", meta-fluorophenethylguanidine, para-fluorophenethylguanidine, ortho-fluorophenethylguanidine, para-fluoro-meta-hydroxy-phenethylguanidine, ortho-fluoro-meta-hydroxyphenethylguanidine, meta-iodophenethylguanidine, and para-hydroxy-meta-iodo-phenethylguanidine. In preferred embodiments, the compounds of the present invention are radio-labeled (e.g., $^{11}$C, $^{14}$C, $^{18}$F, $^{131}$I and $^{123}$I).

In preferred embodiments, the compounds of the present invention are described by the following chemical formula:

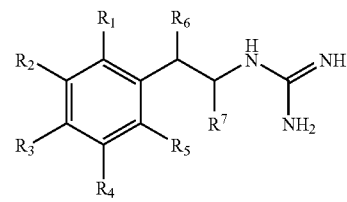

wherein R1, R2, R3, R4 and R5 are the same or different and are selected from the group consisting of H, halogen, hydroxyl, guanyl, methoxy, methyl, amino, and nitro, wherein R6 is selected from the group consisting of H and hydroxyl, and wherein R7 is H or CH$_3$. In preferred embodiments, the compound is selected from the group consisting of [$^{11}$C](−)-β-hydroxyphenethylguanidine, [$^{11}$C]para-methoxy-phenethylguanidine, [$^{11}$C]meta-hydroxyphenethylguanidine, [$^{11}$C]para-hydroxyphenethylguanidine, [$^{11}$C]3,4-dihydroxyphenethylguanidine, "N-[$^{11}$C]guanyl-meta-octopamine", "N-[$^{11}$C]guanyl-norepinephrine", "N-[$^{11}$C]guanyl-(−)-metaraminol", [$^{11}$C]meta-fluorophenethylguanidine, [$^{11}$C]para-fluorophenethylguanidine, [$^{11}$C]ortho-fluorophenethylguanidine, [$^{11}$C]para-fluoro-meta-hydroxy-phenethylguanidine, [$^{11}$C]ortho-fluoro-meta-hydroxy-phenethylguanidine, [$^{11}$C]meta-iodophenethylguanidine, and [$^{11}$C]para-hydroxy-meta-iodo-phenethylguanidine. In preferred embodiments, the halogen is selected from the group consisting of $^{18}$F, $^{211}$At, $^{76}$Br, $^{131}$I, and $^{123}$I.

Additional exemplary embodiments include, but are not limited to:

(1) [$^{18}$F], [$^{76}$Br], [$^{211}$At], [$^{131}$I] or [$^{123}$I]-Phenethylguanidines

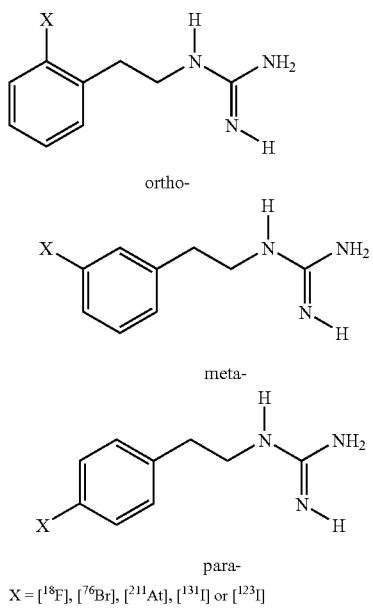

X = [$^{18}$F], [$^{76}$Br], [$^{211}$At], [$^{131}$I] or [$^{123}$I]

(2) [$^{18}$F], [$^{76}$Br], [$^{211}$At], [$^{131}$I] or [$^{123}$I]-3-Hydrophenethylguanidines

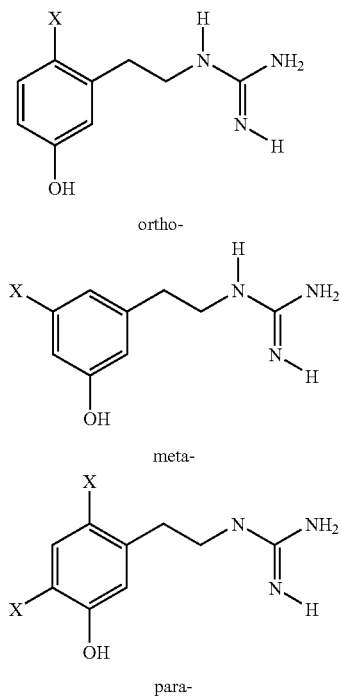

X = [$^{18}$F], [$^{76}$Br], [$^{211}$At], [$^{131}$I] or [$^{123}$I]

(3) [$^{18}$F], [$^{76}$Br]-3,4-Dihydroxyphenethylguanidines

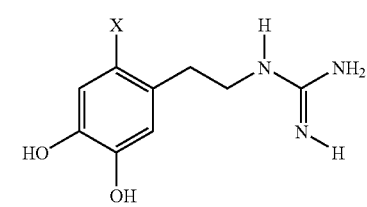

X = [$^{18}$F] or [$^{76}$Br]

(4) [$^{18}$F], [$^{76}$Br], [$^{211}$At], [$^{131}$I] or [$^{123}$I]-β-Hydroxyphenethylguanidines

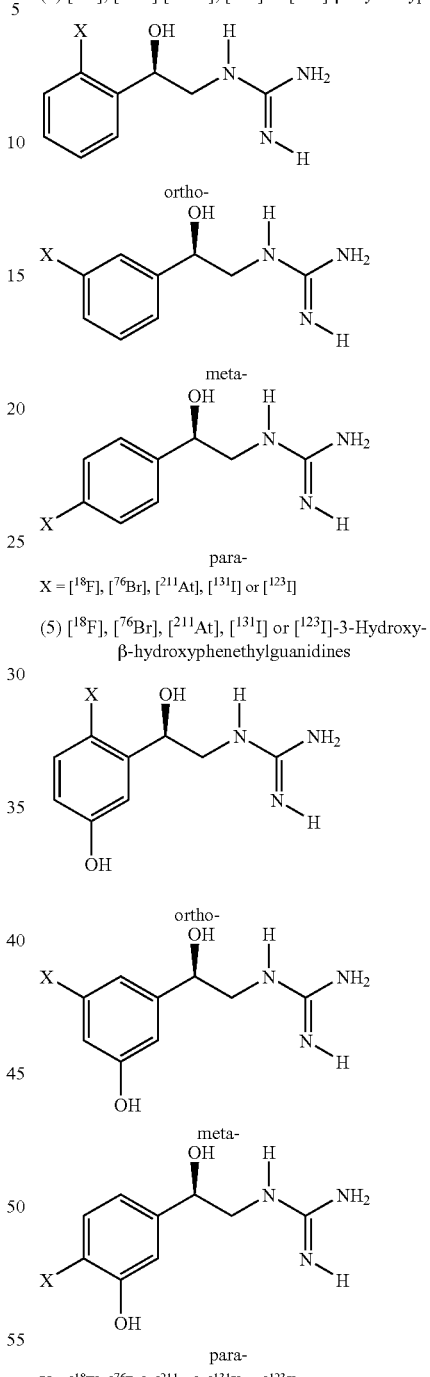

(5) [$^{18}$F], [$^{76}$Br], [$^{211}$At], [$^{131}$I] or [$^{123}$I]-3-Hydroxy-β-hydroxyphenethylguanidines X = [$^{18}$F], [$^{76}$Br], [$^{211}$At], [$^{131}$I] or [$^{123}$I]

II. Uses of Radiotracing Agents

The radiotracing agents of the present invention find many uses. In particular, the radiotracing agents of the present invention find use as imaging agents within nuclear medicine imaging protocols (e.g., PET imaging, SPECT imaging).

In preferred embodiments, the radiotracing agents of the present invention are useful as imaging agents within PET imaging studies. PET is the study and visualization of human physiology by electronic detection of short-lived positron emitting radiopharmaceuticals. It is a non-invasive technology that quantitatively measures metabolic, biochemical and functional activity in living tissue.

The PET scan is a vital method of measuring body function and guiding disease treatment. It assesses changes in the function, circulation and metabolism of body organs. Unlike MRI (Magnetic Resonance Imaging) or CT (Computed Tomography) scans which primarily provide images of organ anatomy, P.E.T. measures chemical changes that occur before visible signs of disease are present on CT and MRI images.

PET visualizes behaviors of trace substances within a subject (e.g., a living body) having an radioimaging agent administered therein by detecting a pair of photons occurring as an electron/positron pair annihilation and flying in directions opposite from each other (see, e.g., U.S. Pat. No. 6,674,083; herein incorporated by reference in its entirety). A PET apparatus is equipped with a detecting unit having a number of small-size photon detectors arranged about a measurement space in which the subject is placed, detects and stores photon pairs occurring as electron/positron pairs annihilation by coincidence counting, and reconstructs an image indicative of a spatial distributions with respect to the frequency of generation of photon pairs in the measurement space, on the basis of the stored number of coincidence-counting information items, or projection data. The PET apparatus play an important role in the field of nuclear medicine and the like, whereby biological functions and higher-order functions of brains can be studied by using it. Such PET apparatus can be roughly classified into two-dimensional PET apparatus, three-dimensional PET apparatus, and slice-septa-retractable type three-dimensional PET apparatus.

In general, a PET detector or camera typically consists of a polygonal or circular ring of radiation detection sensors placed around a patient area (see, e.g., U.S. Pat. No. 6,822,240; herein incorporated by reference in its entirety). Radiation detection begins by injecting isotopes with short half-lives into a patient's body placed within the patient area. The isotopes are absorbed by target areas within the body, and emit positrons. In the human body, the positrons annihilate with electrons. As a result thereof two essentially monoenergetic gamma rays are emitted simultaneously in opposite directions. In most cases the emitted gamma rays leave the body and strike the ring of radiation detectors.

The ring of detectors includes typically an inner ring of scintillation crystals and an outer ring of light detectors, e.g. photomultiplier tubes. The scintillation crystals respond to the incidence of gamma rays by emitting a flash of light (photon energy), so-called scintillation light, which is then converted into electronic signals by a corresponding adjacent photomultiplier tube. A computer, or similar, records the location of each light flash and then plots the source of radiation within the patient's body by comparing flashes and looking for pairs of flashes that arise simultaneously and from the same positron-electron annihilation point. The recorded data is subsequently translated into a PET image. A PET monitor displays the concentration of isotopes in various colors indicating level of activity. The resulting PET image then indicates a view of neoplasms or tumors existing in the patient's body.

Such detector arrangement is known to have a good energy resolution, but relatively bad spatial and temporal resolutions. Early PET detectors required a single photomultiplier tube to be coupled to each single scintillation crystal, while today, PET detectors allow a single photodetector to serve several crystals, see e.g. U.S. Pat. Nos. 4,864,138; 5,451,789; and 5,453,623; each herein incorporated by reference in their entireties). In such manner the spatial resolution is improved or the number of photodetectors needed may be reduced.

Single Photon Emission Computed Tomography (SPECT) is a tomographic nuclear imaging technique producing cross-sectional images from gamma ray emitting radiopharmaceuticals (single photon emitters or positron emitters). SPECT data are acquired according to the original concept used in tomographic imaging: multiple views of the body part to be imaged are acquired by rotating the Anger camera detector head(s) around a craniocaudal axis. Using backprojection, cross-sectional images are then computed with the axial field of view (FOV) determined by the axial field of view of the gamma camera. SPECT cameras are either standard gamma cameras which can rotate around the patient's axis or consist of two or even three camera heads to shorten acquisition time. Data acquisition is over at least half a circle (180°) (used by some for heart imaging), but mostly over a full circle. Data reconstruction has to take into account the fact that the emitted rays are also attenuated within the patient, i. e. photons emanating from deep inside the patient are considerably attenuated by surrounding tissues. While in CT absorption is the essence of the imaging process, in SPECT attenuation degrades the images. Thus, data of the head reconstructed without attenuation correction may show substantial artificial enhancement of the peripheral brain structures relative to the deep ones. The simplest way to deal with this problem is to filter the data before reconstruction. A more elegant but elaborate method used in triple head cameras is to introduce a gamma-ray line source between two camera heads, which are detected by the opposing camera head after being partly absorbed by the patient. This camera head then yields transmission data while the other two collect emission data. Note that the camera collecting transmission data has to be fitted with a converging collimator to admit the appropriate gamma rays.

The Single Photon Emission Computed Tomography (SPECT) is routinely used in clinical studies. SPECT is performed by using a gamma camera, comprising a collimator fixed on a gamma detector, which gamma camera follows a revolution orbit around the patient's body. The gamma rays, emitted by a radioactive tracer, accumulated in certain tissues or organs of the patient's body, are sorted by the collimator and recorded by the gamma detector under various angles around the body, the collimator always pointing to (facing) the rotation axis of the camera. From the acquired planar images the distribution of the activity inside the patient's body can be computed using certain reconstruction algorithms. Generally the so-called Expectation-Maximization of the Maximum-Likelihood (EM-ML) algorithm is used, as described by Shepp et al. (IEEE Trans. Med. Imaging 1982; 2:113-122) and by Lange et al. (J. Comput. Assist. Tomogr. 1984; 8:306-316). This iterative algorithm minimizes the effect of noise in SPECT images.

In preferred embodiments, the radiotracing agents of the present invention are used as imaging agents for PET imaging and SPECT imaging.

It is contemplated that the radiotracing agents of the present invention are provided to a nuclear pharmacist or a clinician in kit form. In accordance, the radiotracing agents can be readily made by a clinician or pharamacist at the location of intended use, thus avoiding shipment of a premade radioiodinated compound.

A pharmaceutical composition of the present invention comprises one of the aforementioned radiotracing agents and a carrier such as a physiological buffered saline solution a physiologically buffered sodium acetate carrier. It is contemplated that the composition will be systemically administered to the patient as by intravenous injection. Suitable dosages for use as a diagnostic imaging agent are, for example, from about 0.2 to about 2.0 mCi of I-131 labeled radiotracing agent for the adrenal medulla or tumors therein, and from about 2.0 to about 10.0 mCi of the I-123 labeled agent for imaging of the heart and adrenal medulla or tumors therein. For use as a therapeutic agent, a higher dosage is required, for example, from about 100 to about 300 mCi of the radiotracing agent material.

It will be appreciated by those skilled in the art that the novel imaging agents of the present invention are employed in accordance with conventional methodology in nuclear medicine in a manner analogous to that of the aforementioned radiotracing agents. Thus, a composition of the present invention is typically systemically applied to the patient, and subsequently the uptake of the composition in the selected organ is measured and an image formed, for example, by means of a conventional gamma camera.

Further understanding of use of the present invention can be obtained from the following examples and from Kline, et al.: "Myocardial Imaging in Man with [123 I]-Meta-Iodobenzylguanidine," J. Nucl. Med. 22:129-132, 1981; Wieland, et al: "Myocardial Imaging with a Radioiodinated Norepinephrine Storage Analog," J. Nucl. Med. 22:22-31, 1981; Valk, et al: "Spectrum of Pheochromocytoma in Multiple Endocrine Neoplasia: A Scintigraphic Portrayal Using sup. 131 I-Meta-Iodobenzylguanidine," Ann. Intern. Med., Vol. 94, pp. 762-767 (1981); Sisson, et al.: "Scintigraphic Localization of Pheochromocytoma," New Eng. J. Med., Vol. 305, pp. 12-17, (1981); and Lynn, et al., "Portrayal of Pheochromocytoma and Normal Human Adrenal Medulla by m-[I-123]-iodobenzylguanidine", J. Nucl. Med., Vol. 25, Vol. 436-440 (1984); and U.S. Pat. Nos. 4,584,187 and 4,622,217; of these articles are specifically incorporated by reference herein.

EXAMPLES

The following examples are provided to demonstrate and further illustrate certain preferred embodiments of the present invention and are not to be construed as limiting the scope thereof.

Example 1

Synthesis and Evaluation of Radiolabeled Phenethylguanidines

To evaluate radiolabeled phenethylguanidines as imaging agents for nuclear medicine, several [$^{11}$C]-labeled phenethylguanidines were synthesized and initial bioevaluations of these compounds performed using an isolated rat heart preparation. The imaging properties of some of these compounds have also been assessed with biodistribution studies in rats. [$^{11}$C]-labeling was used to initially assess the imaging properties of these compounds for the following reasons. A radio-synthetic method for making [$^{11}$C]guanidines (see, e.g., Westerberg, G. and Langstrom, B. (1997) J. Labeled Compds. Radiopharm. 39:525-529; herein incorporated by reference in its entirety), allowed efficient synthesis and evaluation of these compounds.

Initial investigations of radiolabeled phenethylguanidines was divided into 3 groups based on their ultimate radiolabel: [$^{11}$C]phenethylguanidines, [$^{18}$F]phenethylguanidines, and radio-iodinated phenethylguanidines.

TABLE 1

Kinetics of [$^{11}$C]phenethylguanidines in isolated rat heart.

| Series ID# | Name | Acronym | Calc. Log P* | Neuronal Uptake Rate $K_{up}$ (ml/min/g) | Major Clearance Rate $T_{1/2}$ (min) |
|---|---|---|---|---|---|
| | [$^3$H]norepinephrine | NE | −1.74 | 4.44 | >1000 |
| | [$^{11}$C]meta-hydroxyephedrine | HED | 0.31 | 2.35 | 63 |
| | [$^{11}$C]phenylephrine | PHEN | −0.30 | 0.72 | 98 |
| | [$^{11}$C]epinephrine | EPI | −1.34 | 0.60 | 1580 |
| | [$^{11}$C]meta-iodobenzylguanidine | MIBG | 1.33 | 3.65 | 127 |
| | [$^{11}$C]phenethylguanidines: | | | | |
| I-1 | [$^{11}$C]phenethylguanidine | PG | 0.71 | 1.56 | 200 |
| I-2 | [$^{11}$C](−)-β-hydroxyphenethylguanidine | BHPG | −0.27 | 0.42 | 1158 |
| I-3 | [$^{11}$C]para-methoxy-phenethylguanidine | PMPG | 0.63 | 0.73 | 137 |
| I-4 | [$^{11}$C]meta-hydroxyphenethylguanidine | MHPG | −0.02 | 2.12 | trapped |
| I-5 | [$^{11}$C]para-hydroxyphenethylguanidine | PHPG | −0.02 | 1.92 | 2888 |
| I-6 | [$^{11}$C]3,4-dihydroxyphenethylguanidine | DHPG | −0.62 | 1.07 | 1411 |
| I-7 | "N-[$^{11}$C]guanyl-meta-octopamine" | GMO | −0.94† | 0.28 | 13000 |
| I-8 | "N-[$^{11}$C]guanyl-norepinephrine" | GNE | −1.61† | 0.09 | 350 |
| I-9 | "N-[$^{11}$C]guanyl-(−)-metaraminol" | GMR | −0.44 | 0.08 | 1211 |
| | [$^{11}$C]fluorophenethylguanidines: | | | | |
| II-1 | [$^{11}$C]meta-fluorophenethylguanidine | MFPG | 0.84 | 0.24 | 116 |
| II-2 | [$^{11}$C]para-fluorophenethylguanidine | PFPG | 0.84 | 0.63 | 266 |
| II-3 | [$^{11}$C]ortho-fluorophenethylguanidine | OFPG | 0.84 | 1.76 | 135 |
| II-4 | [$^{11}$C]para-fluoro-meta-hydroxy-phenethylguanidine | 4-FHPG | 0.17 | 0.77 | trapped |
| II-5 | [$^{11}$C]ortho-fluoro-meta-hydroxy-phenethylguanidine | 6-FHPG | 0.17 | 0.54 | 1207 |

TABLE 1-continued

Kinetics of [$^{11}$C]phenethylguanidines in isolated rat heart.

| Series ID# | Name | Acronym | Calc. Log P* | Neuronal Uptake Rate $K_{up}$ (ml/min/g) | Major Clearance Rate $T_{1/2}$ (min) |
|---|---|---|---|---|---|
| [$^{11}$C]iodophenethylguanidines: | | | | | |
| III-1 | [$^{11}$C]meta-iodophenethylguanidine | MIPG | 1.75 | 1.10 | 143 |
| III-2 | [$^{11}$C]para-hydroxy-meta-iodo-phenethylguanidine | PHMIPG | 1.08 | | |

*CLOGP of guanidines: ACD Solaris V4.76/ACS SciFinder Scholar.
†Value estimated using QSAR data from Hansch and Leo The [$^{11}$C]-labeled phenethylguanidines of the present invention are summarized in Table 1. Additionally, initial kinetic evaluations in the isolated perfused working rat heart for the [$^{11}$C]-labeled phenethylguanidines are summarized in Table 1. Included are kinetic data for the endogenous neurotransmitter norepinephrine (NE) and several previously developed sympathetic nerve radiotracers including [$^{11}$C] meta-hydroxyephedrine (HED), [$^{11}$C]phenylephrine (PHEN), [$^{11}$C]epinephrine (EPI), and the [$^{11}$C]-labeled analog of MIBG.

The present invention is not limited to a particular mechanism. Indeed, an understanding of the mechanism is not necessary to practice the present invention. Nonetheless, it is contemplated that an effective cardiac sympathetic nerve tracer should possess two properties for it to be a significant improvement over currently available radiotracers: (1) a slow neuronal uptake rate (reflected as a low $K_{up}$ value in the isolated rat heart); and (2) rapid and efficient trapping in storage vesicles inside the neurons (reflected as a very slow clearance half-time ($T_{1/2}$) from the isolated rat heart). Provided below is a detailed description of how these specific kinetic properties offer a significant advantage over currently available sympathetic nerve radiotracers. While a tracer possessing both of these properties would be considered to be 'ideal', it is possible that a tracer with just one of these properties could still represent a significantly better imaging agent due to other factors, such as lower nonspecific uptake in non-target tissues such as the lungs or liver.

Several of the synthesized [$^{11}$C]-labeled phenethylguanidines possess the desired long retention times in the sympathetic neurons of the isolated perfused rat heart, as seen by much longer $T_{1/2}$ values in Table 1. In Group I, compounds I-7 (GMO) and I-9 (GMR) both possess a slow neuronal uptake rate and very long neuronal retention times. Successful compounds from Group II or III would ultimately be radiolabeled with $^{18}$F, $^{123}$I, or $^{131}$I. Other possible radiolabels include radioisotopes of the halogens bromine (Br) and astatine (As).

While a slower neuronal uptake rate is desirable for cardiac sympathetic nerve imaging, for SPECT and PET imaging of adrenergic tumors (e.g., pheochromocytoma and neuroblastoma), a high uptake rate is desirable, since this helps to achieve high tumor/background ratios. To this end, a long retention time is an advantage. Another desirable property for these compounds is low uptake in non-target tissues, especially the liver, which helps in the localization of tumors and metastases in the abdomen. Some of the new fluoro- or iodo-phenethylguanidines have longer retention times than MIBG.

Example 2

PET Imaging of Cardiac Sympathetic Innervation

The imaging agents of the present invention are useful in PET imaging of cardiac sympathetic innervation. Radiotracing agents used for this application include [$^{11}$C]meta-hydroxyephedrine (HED), [$^{11}$C]epinephrine (EPI) and 6-[$^{18}$F] fluorodopamine (FDA). However, the rate at which HED, EPI, and FDA are taken up into sympathetic neurons (e.g., neuronal uptake rate) is too rapid to allow for successful tracer kinetic modeling of respective in vivo kinetics.

A power of PET imaging is an ability to provide accurate quantitative measures of radiotracer tissue concentrations, and from serial measurements of those concentrations over time obtain measurements of the rates of physiological or biochemical processes. Tracer kinetic modeling is a mathematical tool that permits estimation of physiological rates from acquired PET data. Commonly used radiotracing agents (e.g., HED, EPI and FDA) do not intrinsically possess kinetic properties allowing tracer kinetic modeling methods to make desired physiological measurements. Indeed, the compounds described in the present invention (e.g., phenethylguanidines) possess kinetic properties allowing tracer kinetic modeling methods to make desired physiological measurements.

The failure of tracer kinetic modeling methods to work with current radiotracing agents (e.g., HED, EPI, FDA) is due, for example, to the specific Michaelis-Menten transport parameters these compounds possess for the neuronal norepinephrine transporter (NET). All sympathetic nerve radiotracing agents are taken up into sympathetic neurons as 'substrates' for NET. Transport rates of NET substrates are described by the Michaelis-Menten equation, $V_{init}=S_oV_{max}/(K_m+S_o)$, with $S_o$ representing the tracer concentration outside neurons in the synaptic cleft. The true 'tracer' concentrations of substrate in PET imaging studies are used, thereby allowing the assumption that $S_o \ll K_m$ at all times; simplifying the transport rate equation to $V_{init}=(V_{max}/K_m)S_o$. This equation establishes that it is the ratio of a substrate's Michaelis-Menten transport parameters $V_{max}$ and $K_m$ that determines its in vivo neuronal uptake rate. Thus a 'neuronal uptake rate constant' $k_{uptake}=V_{max}/K_m$ can be defined for each NET substrate. Furthermore, the maximum velocity of transport, $V_{max}$, is directly proportional to transporter density.

In diseases in which sympathetic denervation occurs, such as diabetic autonomic neuropathy, NET density will decrease. A decrease in NET density causes $V_{max}$ to decline in direct proportion to reductions in NET density. As such, the value of $k_{uptake}=V_{max}/K_m$ declines in direct proportion to the degree of NET density deficits.

Current sympathetic nerve radiotracing agents (e.g., HED, EPI, FDA) possess very high $V_{max}/K_m$ ratios that lead to very fast neuronal uptake rates in human heart. Tracers that have very rapid uptake into tissue tend to be 'flow-limited' tracers. A problem with a 'flow-limited tracer' in terms of assessing sympathetic nerve density is that nerve losses need to be substantial before the tracer's retention in the heart is reduced from control values. Imaging studies with current sympathetic nerve tracers, which measure only tracer retention, cannot detect nerve losses until they are well below normal. Early detection of denervation is critically important in terms of putting patients on effective therapies to prevent nerve damage. Compounds of the present invention (e.g., phenethylguanidines) possess lower $V_{max}/K_m$ ratios thereby reducing $k_{uptake}$ into a range in which it can be accurately estimated from the PET kinetics. The compounds of the present invention provide clinicians with more sensitive measures of cardiac sympathetic nerve density than are currently possible.

Furthermore, in addition to possessing a slower neuronal uptake rate, there should be sufficient neuronal uptake of the tracer to provide high quality images and low-noise kinetic data. Compounds of the present invention (e.g., phenethylguanidines) are highly retained inside neurons following neuronal uptake.

In preferred embodiments, the radiolabeled phenethylguanidines used in the methods of the present invention possess a slow neuronal uptake, and a long neuronal retention time.

Comparing the kinetic properties of existing tracers (e.g., HED, EPI, FDA) with those of an 'ideal' tracer (e.g., possessing a slow neuronal uptake and a long neuronal retention time), EPI has the slowest neuronal uptake and is rapidly and efficiently stored in vesicles. However, EPI's neuronal uptake rate is fast and it can be metabolized inside the neurons by monoamine oxidase (MAO). While HED is not a MAO substrate, its neuronal uptake rate is too fast and its relatively high lipophilicity leads to poor vesicular retention.

Figure 2:
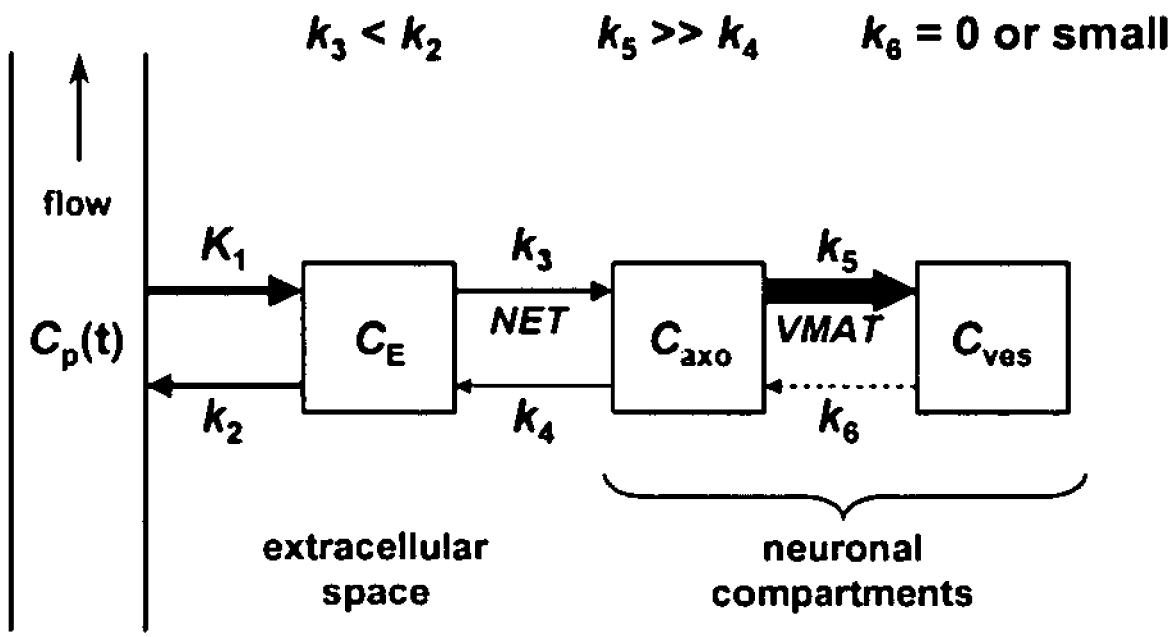
FIG. 2 shows a comprehensive compartmental model for a sympathetic nerve tracer with 'ideal' kinetic properties.

Comprehensive compartmental models for HED and an 'ideal' sympathetic nerve tracer are given in FIGS. 1 and 2. These models are too complex for practical use in fitting data from PET studies since they have too many parameters that need to be estimated simultaneously, but they do describe in detail all of the processes involved in the observed myocardial uptake of the tracers. Arrow thicknesses are drawn in proportion to the magnitude of the rate constants; thick arrows for fast processes and thin arrows for slow processes. Examination of the comprehensive model for HED (see FIG. 1) illustrates a main problem with this tracer in terms of kinetic analyses. The rate of neuronal uptake by NET ($k_3$) is very fast, and is much larger than the rate for clearance back into blood ($k_3 \gg k_2$), so that most of the tracer 'delivered' from blood to the extracellular space (by $K_1$) is very rapidly transported into neurons. The neuronal uptake rate $k_3$ is so fast that the neuronal accumulation of HED is rate-limited by delivery from blood ($K_1$) rather than by NET transport into neurons. Since $K_1=E \cdot F$, where E is the unidirectional extraction fraction and F is blood flow, the tissue accumulation of HED measured with PET is 'flow-limited'.

A fundamental problem with HED is that its neuronal uptake rate ($k_3$) is so fast that its value cannot be estimated from the measured PET kinetics. It can be observed that $k_3$ is a big number, but an exact determination from PET data is not possible. It could be 1.0 min$^{-1}$, 10.0 min$^{-1}$, or possibly 100.0 min$^{-1}$, but since $k_3$ is not 'identifiable' from the PET data, it is impossible to know its value with any degree of accuracy.

Figure 3:
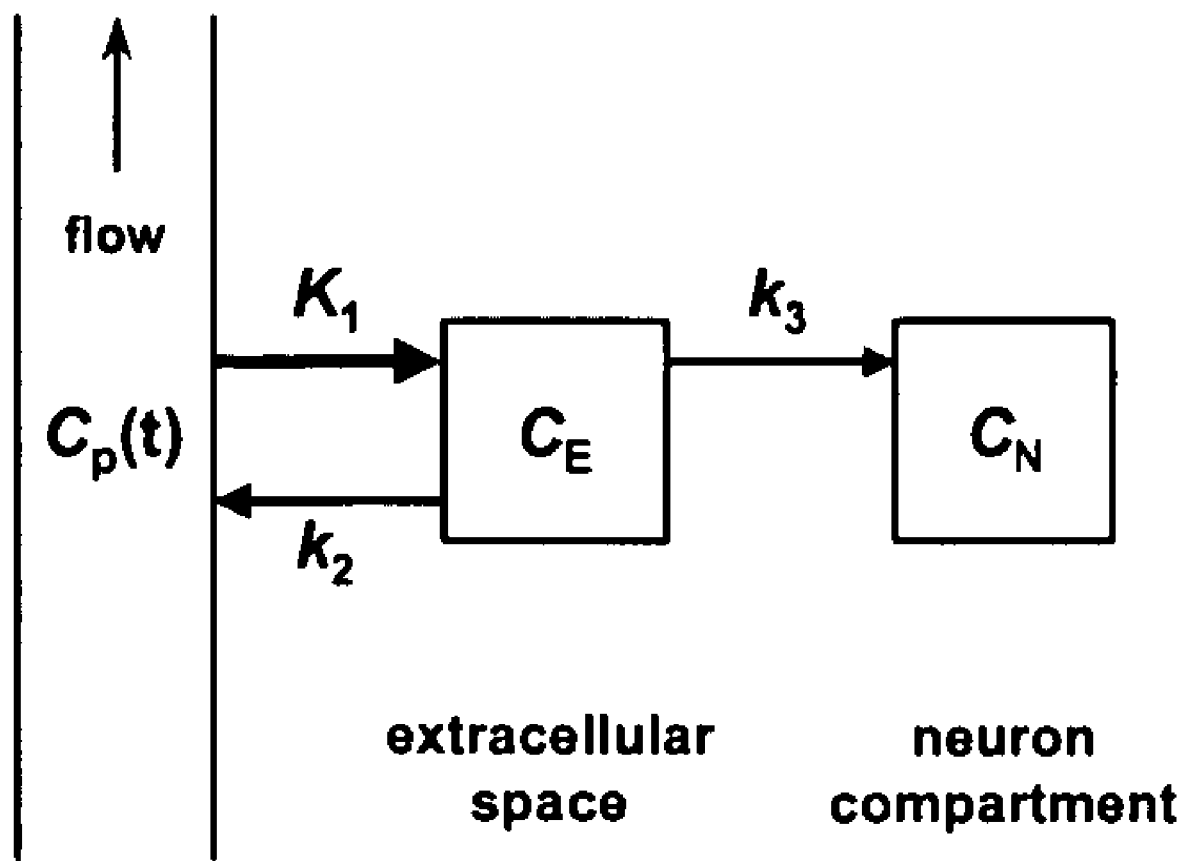
FIG. 3 shows a simplified compartment model for analyzing the PET kinetics of an "ideal" sympathetic nerve tracer.

Conversely, a tracer that inherently possesses 'ideal' kinetic properties (see FIG. 2) can be used to estimate the neuronal uptake rate $k_3$. In this case, neuronal uptake by NET is the rate-limiting step in the neuronal accumulation of the tracer. If the tracer is also rapidly trapped inside vesicles following neuronal uptake, the measured PET kinetics would be exquisitely sensitive to the neuronal uptake rate $k_3$. Thus, if the tracer possesses the desired kinetic properties of slow neuronal uptake ($k_3 < k_2$), rapid vesicular storage ($k_5 \gg k_4$), and efficient vesicular storage ($k_6=0$ or small) (see FIG. 2), then the measured myocardial kinetics can be analyzed with a simplified compartmental model (see FIG. 3). This model is used to estimate four model parameters from the myocardial PET kinetics: $K_1$, $k_2$, $k_3$, and a blood volume fraction term, BV. Note that this approach allows separate estimation of the parameters $K_1$ and $k_3$. Thus, it is possible to separate the effects of blood flow (contained in $K_1=E \cdot F$) from the tracer's neuronal uptake rate ($k_3$). Again, since $k_3$ is equal to $V_{max}/K_m$, and $V_{max}$ is directly proportional to NET density, this estimated value of $k_3$ is a sensitive measure of myocardial sympathetic nerve density.

Since an 'ideal' tracer is trapped inside neurons following its slow neuronal uptake, rendering the neuron compartment an 'irreversible compartment', a tracer's kinetics could alternatively be analyzed using the Patlak graphical method (see, e.g., Patlak, C. S. and Blasberg, R. G. (1985) J. Cereb. Blood Flow 5: 584-590; herein incorporated by reference in its entirety). The equation for the 'Patlak slope' for an ideal tracer is given by Equation 1.

Equation 1:
$$K_{patlak} = \frac{K_1 k_3 k_5}{k_2(k_4+k_5)+k_3 k_5}$$

Since an ideal tracer has the property $k_5 \gg k_4$, this makes $(k_4+k_5) \approx k_5$. This allows a simplification of the Patlak equation such that the $(k_4+k_5)$ term in the denominator is replaced with $k_5$ as shown in Equation 2.

Equation 2:
$$K_{patlak} \cong \frac{K_1 k_3 k_5}{k_2(k_5)+k_3 k_5} = \frac{K_1 k_3}{k_2+k_3}$$

This leads to the observation that the Patlak slope for a tracer with the 'ideal' kinetic properties is only sensitive to the rate constants $K_1$, $k_2$, and $k_3$. This confirms that a tracer with an 'ideal' property could be analyzed with the model shown in FIG. 3, since this model would predict the same Patlak slope shown in Equation 2. Examination of Equation 2 emphasizes why $k_3 < k_2$ is desired. If $k_3$ is much larger than $k_2$, then the Patlak slope approaches $K_1$, indicating a flow-limited tracer. On the other hand, if the value of $k_3$ is in the range of $(0.05) k_2-(0.5)k_2$, then the denominator of the Patlak slope equation is dominated by $k_2$. Under these conditions, the Patlak slope would tend to track linearly with reductions in $k_3$. Since $k_3$ is equal to $V_{max}/K_m$, and $V_{max}$, is directly proportional to NET density, the Patlak slope of an ideal tracer would track linearly with NET density.

Figure 4:
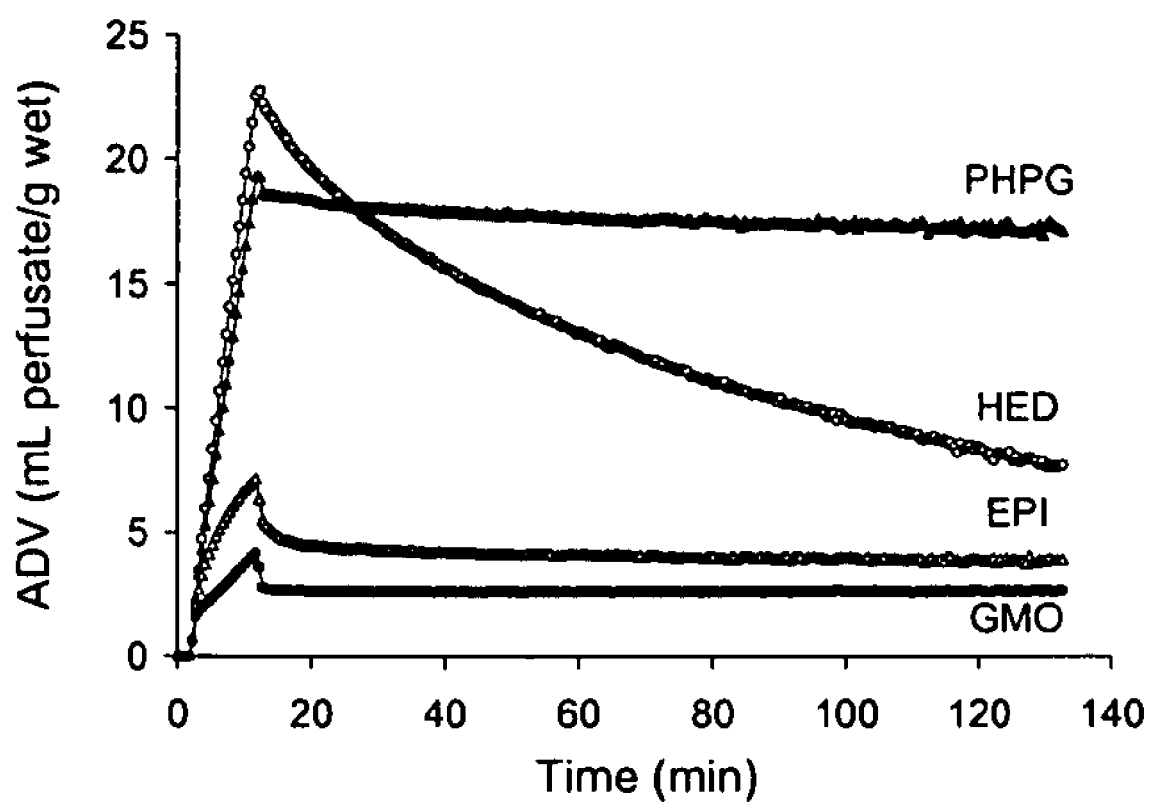
FIG. 4 shows a comparison of the neuronal uptake and retention of the [$^{11}C$]phenethylguanidines PHPG and GMO with those of HED and EPI, in the isolated rat heart. ADV: "apparent distribution volume".

The [$^{11}$C]phenethylguanidines of the present invention possess a slow neuronal uptake, and a long neuronal retention time. FIGS. 4-7 show tracer uptake and retention in cardiac sympathetic neurons for several [$^{11}$C]phenethylguanidines using an isolated perfused rat heart system. In FIG. 4, the kinetics of compounds I-5 (PHPG) and I-7 (GMO) in the isolated rat heart are compared with those of the clinically used PET radiotracers HED and EPI. Both PHPG and GMO are well retained inside cardiac sympathetic neurons.

Figure 5:
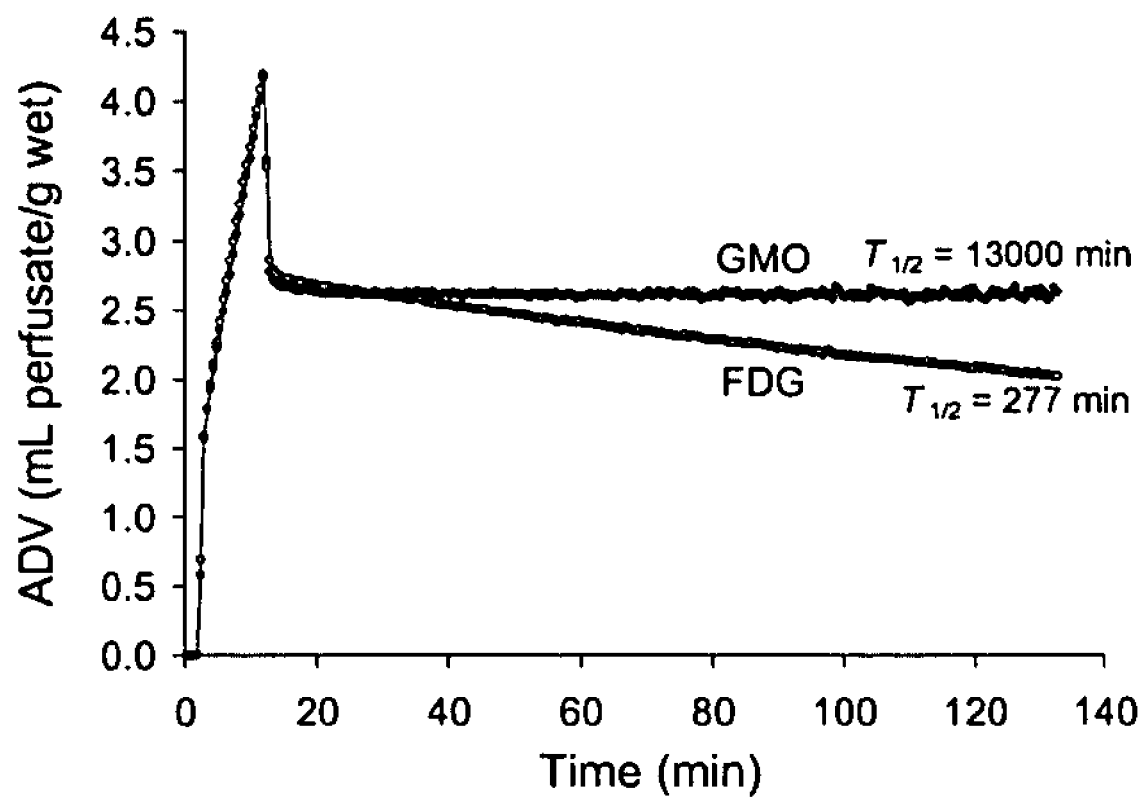
FIG. 5 shows a comparison of the neuronal kinetics of GMO and the myocardial kinetics of the glucose analog [$^{18}F$] FDG (10 mM glucose, no insulin) in the isolated rat heart.

In FIG. 5, the kinetics of GMO are compared with the kinetics of 2-[$^{18}$F]fluoro-2-deoxy-D-glucose (FDG) in the isolated rat heart. The neuronal uptake rate of GMO (0.28 ml/min/g wet) is so close to the myocardial uptake rate of FDG (0.31 ml/min/g wet) that the two uptake curves lay almost on top of each other during the 10 min constant infusion period. Comparing the clearance rates of GMO and FDG indicates that the neuronal trapping of GMO is more efficient than the myocardial trapping of FDG. This similarity of GMO and FDG kinetics in the isolated rat heart is very encouraging from a kinetic modeling perspective, since it supports the hypothesis that the in vivo kinetics of a tracer like GMO can be quantitatively analyzed with compartmental modeling analysis or with Patlak graphical analysis, the same methods that are used to analyze the myocardial kinetics of FDG in human PET studies (see, e.g., Gambhir, et al. (1989) J. Nucl. Med. 30:359-366; herein incorporated by reference in its entirety).

Figure 6:
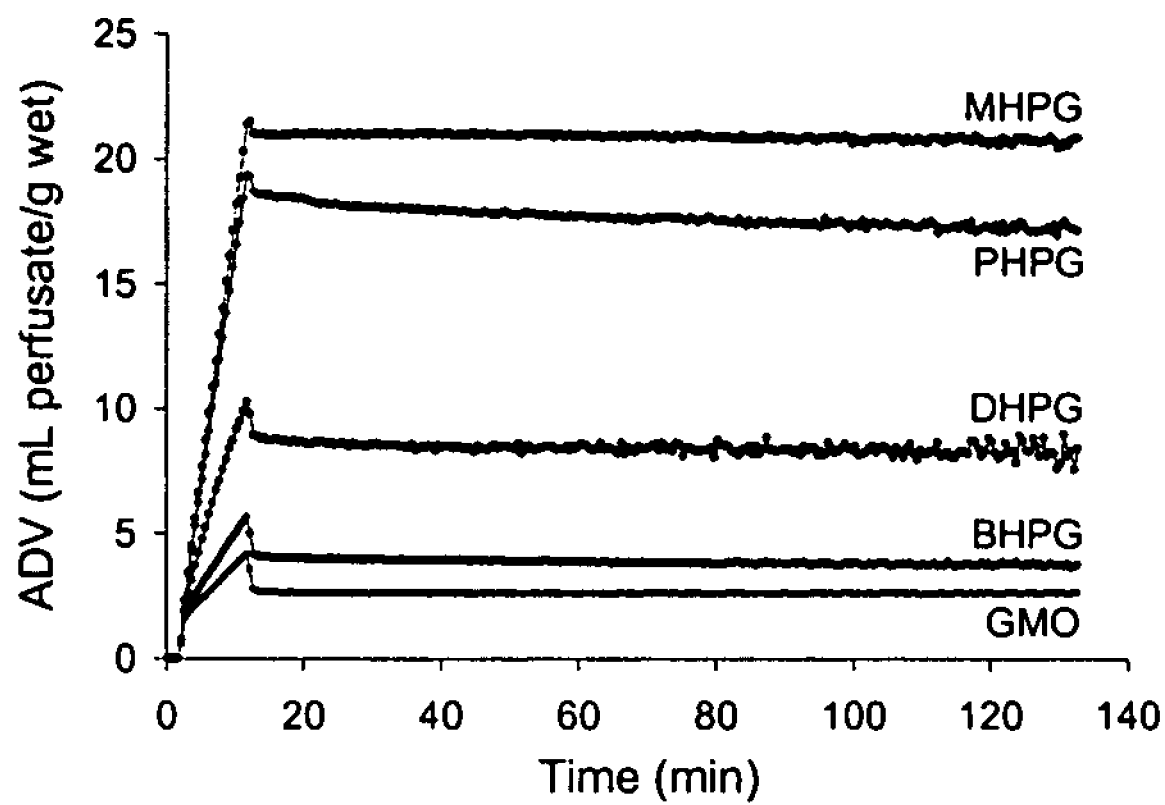
FIG. 6 shows neuronal kinetics of the [$^{11}C$]phenethylguanidines MHPG, PHPG, DHPG, BHPG and GMO in the isolated rat heart. Note the very long neuronal retention times of these agents, which is due to trapping of the tracers inside storage vesicles.

In FIG. 6, the kinetics of several [$^{11}$C]phenethylguanidines are shown. All of these compounds are highly retained inside norepinephrine storages vesicles inside the neurons, effectively trapping the tracers intraneuronally. Although some of the compounds have neuronal uptake rates that remain too fast for kinetic modeling methods to succeed, some of the compounds do have slower neuronal uptake rates and show high potential of being successful tracer for quantifying cardiac sympathetic nerve density using PET imaging. In particular, compounds I-7 (GMO) and I-9 (GMR) (see Table 1) each have very long neuronal retention times as well as neuronal uptake rates that are slower than all currently used tracers. Furthermore, some of the compounds with fast neuronal uptake rates and efficient vesicular storage, such as compounds I-4 (MHPG) and I-5 (PHPG) prove to be very useful in imaging of adrenergic tumors using PET.

Figure 7:
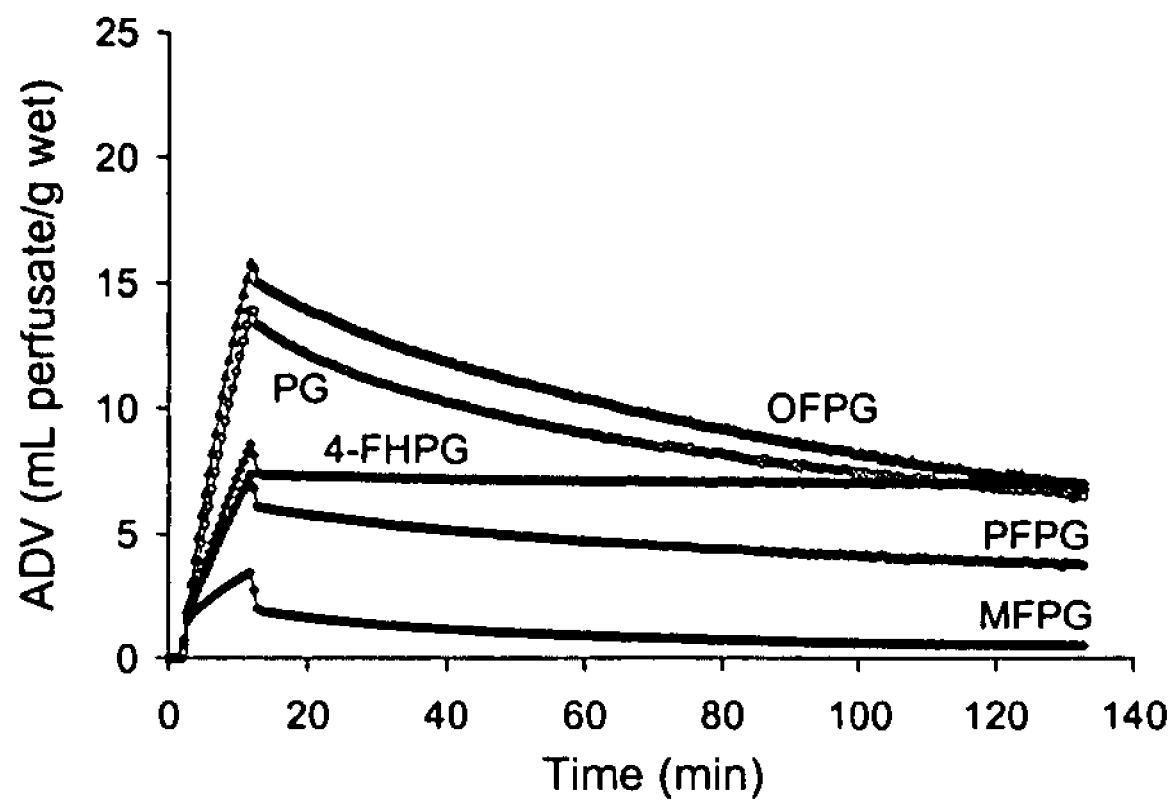
FIG. 7 shows neuronal kinetics of the unsubstituted reference molecule [$^{11}C$]phenethylguanidine (PG) and its ring-fluorinated analogs ortho-fluoro-PG (OFPG), para-fluoro-PG (PFPG), meta-fluoro-PG (MFPG), & 4-fluoro-meta-hydroxy-PG (4-FHPG).

In FIG. 7, the kinetics of several [$^{11}$C]fluorophenethylguanidines are compared with those of the unsubstituted reference molecule I-1 (PG). Compounds II-4 (4-FHPG) and II-5 (6-FHPG), possess very long neuronal retention times (see Table 1). Results with these compounds provide designs comprising a ring-fluorinated phenethylguanidine with a slower neuronal uptake rate that is highly retained in vesicles.

The present invention is not limited to a particular mechanism. Indeed, an understanding of the mechanism is not necessary to practice the present invention. Nonetheless, an [$^{18}$F]-labeled fluorophenethylguanidine with optimal kinetic properties for PET imaging, thus providing quantitative regional estimates of cardiac sympathetic nerve density in patients, finds use as a clinically important tool for physicians.

Currently available PET radiotracers for imaging cardiac sympathetic innvervation are taken up into sympathetic neurons at such a rapid rate that application of tracer kinetic modeling methods fail. Furthermore, the rapid uptake makes measures of tracer retention relatively insensitive to nerve density, since tracer retention does not begin to decline until nerve losses become rather severe. A new sympathetic nerve tracer with two 'ideal' kinetic properties: (1) a slower neuronal uptake rate; and (2) rapid trapping inside storage vesicles, allows tracer kinetic modeling methods to succeed. This allows estimation of a model rate constant that provides an accurate measure of cardiac sympathetic nerve density. Since clinicians are able to obtain accurate and sensitive measurements of cardiac sympathetic nerve density in all regions of the left ventricle in the living human heart, this provides a clinically important tool. The additional accuracy and sensitivity these new radiotracers provide represent a substantial improvement over currently available sympathetic nerve tracers.

Example 3

PET Imaging of Adrenergic Tumors

Interest in using PET imaging for the localization of adrenergic tumors such as pheochromocytoma and neuroblastoma has begun to increase in recent years. To date, the PET tracers that have been used clinically for this particular application include HED (see, e.g., Shulkin, B. L. et al. (1992) J. Nucl. Med. 33:1125-1131; Shulkin, B. L. et al. (1996) J. Nucl. Med. 37:16-21; each of which is herein incorporated by reference in their entireties), 2-[$^{18}$F]fluoro-2-deoxy-D-glucose (FDG) (see, e.g., Shulkin, B. L. et al. (1999) Radiology 212: 35-41; herein incorporated by reference in its entirety), and 6-[$^{18}$F]fluorodopamine (6-FDA) (see, e.g., Ilias, I. et al. (2003) J. Clin. Endocrinol. Metab. 88:4083-4087; herein incorporated by reference in its entirety). Additionally, para-[$^{18}$F]fluorobenzylguanidine (PFBG) has been used to image pheochromocytoma in dogs (see, e.g., Berry, C. R. et al. (2002) Vet. Radiol. Ultrasound 43:183-186; herein incorporated by reference in its entirety). When compared to SPECT imaging with MIBG, it is contemplated that both FDG and 6-FDA provide advantages in terms of increased 'sensitivity' of tumor detection.

With the ever-increasing number of stand-alone PET centers devoted to cancer imaging studies with [$^{18}$F]-labeled tracers such as FDG, this clinical application is an important one for a successful [$^{18}$F]-labeled phenethylguanidine with good imaging characteristics for localizing adrenergic tumors. For this application, fast uptake rates are desired because they increase tumor uptake of the tracer. The present invention is not limited to a particular mechanism. Indeed, an understanding of the mechanism is not necessary to practice the present invention. Nonetheless, compounds with good vesicular uptake are best suited for this application for the following reasons. First, it is likely that compounds that are well transported into vesicles will tend to accumulate better inside the tumors and stay there for very longer periods of time. This would lead to higher accumulation of tracer in the tumors than a tracer with poor vesicular uptake. Also, the resulting long retention times in the tumors would allow more time for "non-specific" binding of the tracers to clear before performing the imaging portion of the study, increasing tumor-to-background ratios. However, the specific mechanisms involved in the retention of compounds like MIBG and 6-FDA in these tumors are still not completely understood, nor need they be for the practice of the present invention.

The present invention is not limited to a particular mechanism. Indeed, an understanding of the mechanism is not necessary to practice the present invention. Nonetheless, a practical advantage of using a PET tracer vs. MIBG and SPECT imaging for this application is that the patient could be injected with the radiotracer and imaged on the same day. Currently, MIBG must be injected at least 24 hours before the imaging study. This would make the process more convenient for the patients, eliminating the need for an overnight stay.

I-4 ([$^{11}$C]meta-hydroxy-phenethylguanidine; MHPG) and I-5 ([$^{11}$C]para-hydroxy-phenethylguanidine; PHPG) possess rapid uptake rate and very long retention times.

On the other hand, a successful [$^{18}$F]fluorophenethylguanidine could enjoy widespread clinical use as a tracer for localizing adrenergic tumors using PET imaging, much as MIBG and SPECT imaging is used today. The present invention is not limited to a particular mechanism. Indeed, an understanding of the mechanism is not necessary to practice the present invention. Nonetheless, compounds such as II-3 (ortho-[$^{18}$F]fluorophenethylguanidine) and II-4 ([$^{18}$F]-para-fluoro-meta-hydroxy-phenethylguanidine) find use as tracers for this application.

Example 4

SPECT Imaging of Cardiac Sympathetic Innervation

The tracer currently used world-wide for this application is [$^{123}$I]meta-iodobenzylguanidine (MIBG). Because of its very rapid neuronal uptake (see Table 1), it is likely that cardiac MIBG retention is also a relatively insensitive measure of nerve density in early cardiac denervation. Since SPECT imaging is a semi-quantitative method, true quantitation of nerve density using tracer kinetic modeling with a radio-iodinated tracer possessing 'ideal' kinetic properties is not currently possible. However, a radio-iodinated phenethylguanidine with a slower neuronal uptake rate than MIBG is contemplated to provide more sensitive measures of nerve density than are currently possible using SPECT imaging. Long neuronal retention times in this application would be desirable, but not necessary, for a new tracer to be clinically superior to MIBG.

meta-iodophenethylguanidine (MIPG) has a neuronal uptake rate that is around 3 times slower than MIBG (see Table 1). MIPG clears from cardiac sympathetic neurons in the perfused rat heart at approximately the same rate as MIBG. The present invention is not limited to a particular mechanism. Indeed, an understanding of the mechanism is not necessary to practice the present invention. Nonetheless, this indicates that MIPG is a more sensitive tracer for detecting myocardial denervation than MIBG. MIPG is better suited to cardiac imaging than MIBG due to its slower neuronal uptake rate. In particular, an analog of MIPG possessing significantly lower lipophilicity (i.e., a lower Log P value) will possess less nonspecific uptake in tissues such as the lung and liver, which also provides an improvement in terms of providing clearer images of the heart using SPECT imaging.

All publications and patents mentioned in the above specification are herein incorporated by reference. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

What is claimed is:

1. A composition comprising a radio-labeled compound, wherein said radio-labeled compound is selected from the group consisting of
[$^{11}$C](−)-β-hydroxyphenethylguanidine,
[$^{11}$C]para-methoxy-phenethylguanidine,
[$^{11}$C]meta-hydroxyphenethylguanidine,
[$^{11}$C]para-hydroxyphenethylguanidine,
[$^{11}$C]3,4dihydroxyphenethylguanidine,
N-[$^{11}$C]guanyl-meta-octopamine,
N-[$^{11}$C]guanyl-norepinephrine,
N-[$^{11}$C]guanyl-(−)-metaraminol,
[$^{14}$C](−)-β-hydroxyphenethylguanidine,
[$^{14}$C]para-methoxy-phenethylguanidine,
[$^{14}$C]meta-hydroxyphenethylguanidine,
[$^{14}$C]para-hydroxyphenethylguanidine,
[$^{14}$C]3,4-dihydroxyphenethylguanidine,
N-[$^{14}$C]guanyl-meta-octopamine,
N-[$^{14}$C]guanyl-norepinephrine,
N-[$^{14}$C]guanyl-(−)-metaraminol,
meta-[$^{18}$F]fluorophenethylguanidine,
para-[$^{18}$F]fluorophenethylguanidine,
ortho-[$^{18}$F]fluorophenethylguanidine,
para-[$^{18}$F]fluoro-meta-hydroxy-phenethylguanidine,
ortho-[$^{18}$F]fluoro-meta-hydroxy-phenethylguanidine,
para-hydroxy-meta-[$^{123}$I]iodo-phenethylguanidine,
para-hydroxy-meta-[$^{124}$I]iodo-phenethylguanidine, and
para-hydroxy-meta-[$^{131}$I]iodo-phenethylguanidine.

2. A radio-labeled compound comprising the following structure:

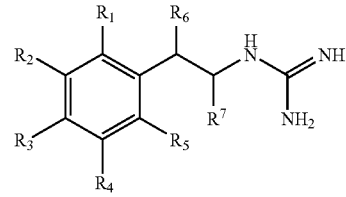

wherein said radio-labeled compound is selected from the group consisting of a [$^{11}$C] radio-labeled compound, a [$^{14}$C] radio-labeled compound, a [$^{18}$F] radio-labeled compound, a [$^{211}$At] radio-labeled compound, a [$^{76}$BR] radio-labeled compound, a [$^{131}$I] radio-labeled compound, a [$^{124}$I] radio-labeled compound, and a [$^{123}$I] radio-labeled compound, wherein R1, R2, R3, R4 and R5 are the same or different and are selected from the group consisting of H, halogen, hydroxyl, guanyl, methoxy, methyl, amino, and nitro, wherein R6 is selected from the group consisting of H and hydroxyl, wherein at least one of R2, R3, R4 and R6 is hydroxyl, and wherein R7 is H or CH$_3$.

3. The compound of claim 2, wherein said radio-labeled compound is selected from the group consisting of
[$^{11}$C](−)-β-hydroxyphenethylguanidine,
[$^{11}$C]meta-hydroxyphenethylguanidine,
[$^{11}$C]para-hydroxyphenethylguanidine,
[$^{11}$C]3,4-dihydroxyphenethylguanidine,
N-[$^{11}$C]guanyl-meta-octopamine,
N-[$^{11}$C]guanyl-norepinephrine,
N-[$^{11}$C]guanyl-(−)-metaraminol,
[$^{14}$C](−)-β-hydroxyphenethylguanidine,
[$^{14}$C]meta-hydroxyphenethylguanidine,
[$^{14}$C]para-hydroxyphenethylguanidine,
[$^{14}$C]3,4-dihydroxyphenethylguanidine,
N-[$^{14}$C]guanyl-meta-octopamine,
N-[$^{14}$C]guanyl-norepinephrine,
N-[$^{11}$C]guanyl-(−)-metaraminol,
para-[$^{18}$F]fluoro-meta-hydroxy-phenethylguanidine,
ortho-[$^{18}$F]fluoro-meta-hydroxy-phenethylguanidine,
para-hydroxy-meta-[$^{123}$I]iodo-phenethylguanidine,
para-hydroxy-meta-[$^{124}$I]iodo-phenethylguanidine, and
para-hydroxy-meta-[$^{131}$I]iodo-phenethylguanidine.

4. An imaging composition comprising the radio-labeled compound described in claim 2.

5. A method of imaging an organ comprising:
(a) applying a composition to a subject, wherein said composition comprises a radio-labeled compound selected from the group consisting of:
1) a compound described by Formula A, wherein Formula A is represented by:

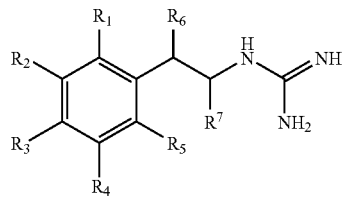

wherein said compound is selected from the group consisting of a [$^{11}$C] radio-labeled compound, a [$^{18}$F] radio-labeled compound, a [$^{211}$At] radio-labeled compound, a [$^{76}$BR] radio-labeled compound, a [$^{131}$I] radio-labeled compound, a [$^{124}$I] radio-labeled compound, and a [$^{123}$I] radio-labeled compound, wherein R1, R2, R3, R4 and R5 are the same or different and are selected from the group consisting of H, halogen, hydroxyl, guanyl, methoxy, methyl, amino, and nitro, wherein R6 is selected from the group consisting of H and hydroxyl, wherein at least one of R2, R3, R4 and R6 is hydroxyl, and wherein R7 is H or CH$_3$; and
2) a compound selected from the group consisting of:
[$^{11}$C](−)-β-hydroxyphenethylguanidine,
[$^{11}$C]para-methoxy-phenethylguanidine,
[$^{11}$C]meta-hydroxyphenethylguanidine,
[$^{11}$C]para-hydroxyphenethylguanidine,
[$^{11}$C]3,4-dihydroxyphenethylguanidine,
N-[$^{11}$C]guanyl-meta-octopamine,
N-[$^{11}$C]guanyl-norepinephrine,
N-[$^{11}$C]guanyl-(−)-metaraminol,
meta-[$^{18}$F]fluorophenethylguanidine,
para-[$^{18}$F]fluorophenethylguanidine,
ortho-[$^{18}$F]fluorophenethylguanidine,
para-[$^{18}$F]fluoro-meta-hydroxy-phenethylguanidine,
ortho-[$^{18}$F]fluoro-meta-hydroxy-phenethylguanidine,
para-hydroxy-meta-[$^{123}$I]iodo-phenethylguanidine,
para-hydroxy-meta-[$^{124}$I]iodo-phenethylguanidine, and
para-hydroxy-meta-[$^{131}$I]iodo-phenethylguanidine, and
(b) detecting gamma radiation emitted by said composition and forming an image therefrom.

6. The method of claim 5, wherein said organ is selected from the group consisting of the heart, adrenal medulla, and tumors of the adrenal medulla.

7. The method of claim 5, wherein said imaging is PET imaging.

8. The method of claim 5, wherein said imaging is SPECT imaging.

9. The method of claim 5, wherein said compound described by Formula A is selected from the group consisting of
[$^{11}$C](−)-β-hydroxyphenethylguanidine,
[$^{11}$C]meta-hydroxyphenethylguanidine,
[$^{11}$C]para-hydroxyphenethylguanidine,
[$^{11}$C]3,4-dihydroxyphenethylguanidine,
N-[$^{11}$C]guanyl-meta-octopamine,
N-[$^{11}$C]guanyl-norepinephrine,
N-[$^{11}$C]guanyl-(−)-metaraminol,
para-[$^{18}$F]fluoro-meta-hydroxy-phenethylguanidine,
ortho-[$^{18}$F]fluoro-meta-hydroxy-phenethylguanidine,
para-hydroxy-meta-[$^{123}$I]iodo-phenethylguanidine
para-hydroxy-meta-[$^{124}$I]iodo-phenethylguanidine, and
para-hydroxy-meta-[$^{131}$I]iodo-phenethylguanidine.

10. An imaging composition comprising the radio-labeled compound described in claim 1.

11. The method of claim 5, wherein said imaging is obtained with a gamma camera.

* * * * *